United States Patent [19]

Selliah

[11] Patent Number: 5,814,660
[45] Date of Patent: Sep. 29, 1998

[54] 9-OXA PROSTAGLANDIN ANALOGS AS OCULAR HYPOTENSIVES

[75] Inventor: Robert D. Selliah, Fort Worth, Tex.

[73] Assignee: Alcon Laboratories, Inc., Fort Worth, Tex.

[21] Appl. No.: 878,030

[22] Filed: Jun. 18, 1997

Related U.S. Application Data

[63] Continuation-in-part of PCT/US96/17900, Nov. 12, 1996.

[60] Provisional application No. 60/009,866 Dec. 22, 1995.

[51] Int. Cl.$^6$ .................................................. A61K 31/34
[52] U.S. Cl. ........................ 514/461; 514/473; 514/912; 549/475; 549/497
[58] Field of Search .................... 514/461, 473, 514/912; 549/475, 497

[56] References Cited

U.S. PATENT DOCUMENTS

| | | | |
|---|---|---|---|
| 3,883,659 | 5/1975 | Vlattas | 424/285 |
| 4,088,779 | 5/1978 | Vlattas | 424/285 |
| 4,133,817 | 1/1979 | Lourens et al. | 260/340.9 P |
| 4,133,948 | 1/1979 | Lourens et al. | 536/1 |
| 4,599,353 | 7/1986 | Bito et al. | 514/530 |
| 5,321,128 | 6/1994 | Stjernschantz et al. | 514/530 |
| 5,574,066 | 11/1996 | Chan et al. | 514/548 |

FOREIGN PATENT DOCUMENTS

| | | |
|---|---|---|
| 0561073 A1 | 9/1993 | European Pat. Off. . |
| 0667160 A2 | 8/1995 | European Pat. Off. . |
| 0686628 A2 | 12/1995 | European Pat. Off. . |
| 2460977 A1 | 1/1976 | Germany . |
| 2601333 A1 | 7/1976 | Germany . |
| 2618861 A1 | 11/1976 | Germany . |
| 2739277 A1 | 3/1978 | Germany . |
| 4229050 A1 | 3/1994 | Germany . |
| 1458164 | 12/1976 | United Kingdom . |
| 1539364 | 1/1979 | United Kingdom . |
| WO 95/26729 | 10/1995 | WIPO . |

OTHER PUBLICATIONS

Alm, "The Potential of Prostaglandin Derivatives in Glaucoma Therapy" *Current Opinion in Ophthalmology* 4(11):44–50 (1993).

Arndt et al., "Stereospecific Synthesis of Modified Prostaglandins Derived from Carbohydrates. Part 1." *S. Afr. J. Chem.* 34(4):121–127 (Jun. 1981).

Bock, et al. "Acid Catalyzed Dehydratin of Alditols. Part I. $_D$–Glucitol and $_D$–Mannitol" *Acta Chemica Scandinavica B* 35:441–449 (1981).

Giuffre, "The Effects of Prostaglandin $F_{2\alpha}$ the Human Eye" *Graefe's Arch Clin Exp Ophthalmol* 222:139–141 (1985).

Hanessian et al., "Total Synthesis of 11–Oxaprostaglandin $F_{2\alpha}$ and $F_{2\beta}$," *Carbohydrate Research* 141(2):221–238 XP000644751 (1985).

Kerstetter et al., "Prostaglandin $F_{2\alpha}$–1–Isopropylester Lowers Intraocular Pressure Without Decreasing Aqueous Humor Flow" *American Journal of Ophthalmology* 105:30–34 (1988).

Thierauch et al., "Prostaglandins and Their Receptors: II. Receptor Structure and Signal Transduction" *Journal of Hypertension* 12:1–5 (1994).

Verdoorn et al., "Synthesis of Methyl(5Z, 13E(15S)–9α–acetoxy–15–hydroxy–17–(3–trifluoromethylphenyl)–11–oxa–18,19,20–trinorprosta–5,13–dienoate" *S. Afr. Tydskr. Chem.* 40(2):134–138 XP000618452 (1987).

Vlattas et al., "Synthesis of 9–Oxaprostaglandins" *Tetrahedron Letters* No. 51/52:4455–4458, Pergamon Press, 1974.

Vlattas et al., "Synthesis of 11–oxaprostaglandins" *Tetrahedron Letters* No. 51/52:4451–4454, XP000644759, Pergamon Press, 1974.

*Primary Examiner*—Amelia Owens
*Attorney, Agent, or Firm*—Barry L. Copeland

[57] ABSTRACT

Substituted tetrahydrofuran analogs of prostaglandins and methods of their use in treating glaucoma and ocular hypertension are disclosed.

19 Claims, No Drawings

9-OXA PROSTAGLANDIN ANALOGS AS OCULAR HYPOTENSIVES

CROSS-REFERENCE TO RELATED APPLICATIONS

The present application is a continuation-in-part of an earlier filed pending application, International Application Ser. No. PCT/US96/17900, filed Nov. 12, 1996, which International Application draws priority from U.S. Provisional Application Ser. No. 60/009,866, filed Dec. 22, 1995.

BACKGROUND OF THE INVENTION

The present invention relates to novel compounds and compositions, and methods of their use in the treatment of glaucoma and ocular hypertension. In particular, the present invention relates to the use of certain substituted tetrahydrofuran analogs of D and F series prostaglandins to treat glaucoma and ocular hypertension.

Glaucoma is a progressive disease which leads to optic nerve damage, and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which reduce either the production of aqueous humor within the eye, such as beta-blockers and carbonic anhydrase inhibitors, or increase the flow of aqueous humor out of the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics may cause tachycardia, arrhythmia and hypertension. There is therefore a continuing need for therapies which control the elevated intraocular pressure associated with glaucoma.

Prostaglandins, which are metabolite derivatives of arachidonic acid, have recently been pursued for possible efficacy in lowering IOP. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-series prostaglandins (EP 0 561 073 A1). Of interest in the present invention are compounds which are believed to exhibit IOP lowering mechanisms similar to those exhibited by $PGD_2$ (formula I) and $PGF_{2\alpha}$ (formula II):

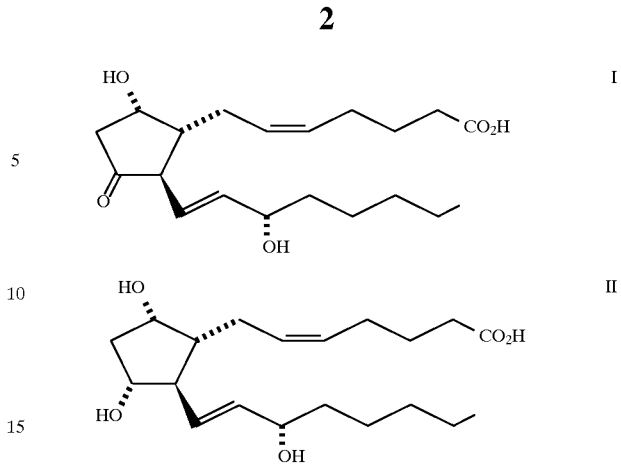

The relationship between prostaglandin DP receptor activation and IOP lowering effects is not well understood. Various publications have reported that DP receptor activation leads to second messenger activation and in particular, to the stimulation of adenylate cyclase and resultant increases in cAMP levels (Thierauch, Prostaglandins and their Receptors: II. Receptor Structure and Signal Transduction, *Journal of Hypertension*, volume 12, pages 1–5 (1994). Regardless of mechanism, $PGD_2$ has been shown to lower IOP (Nakajima, Effects of Prostaglandin $D_2$ and its analog, BW245C, on Intraocular Pressure in Humans, *Graefe's Archive Ophthalmology*, volume 229, pages 411–413 (1991)). Thus, it has been of interest in the field to develop synthetic $PGD_2$ analogs with IOP lowering efficacy.

Synthetic $PGD_2$-type analogs have been pursued in the art (*Graefe's Archive Ophthalmology*, volume 229, pages 411–413 (1991)). Though some $PGD_2$-type molecules lower IOP, these types of molecules have also been associated with undesirable side effects resulting from topical ophthalmic dosing. Such effects have included an initial increase in IOP, conjunctival hyperemia, increases in microvascular permeability, and increases in eosinophile infiltration (Alm, The Potential of Prostaglandin Derivatives in Glaucoma Therapy, *Current Opinion in Ophthalmology*, volume 4, No. 11, pages 44–50 (1993)).

Similarly, the relationship of prostaglandin FP receptor activation and IOP lowering effects is not well understood. It is believed that FP receptor activation leads to increased outflow of aqueous humor. Regardless of mechanism, $PGF_{2\alpha}$ and some of its analogs have been shown to lower IOP (Giuffre, The Effects of Prostaglandin $F_{2\alpha}$ the Human Eye, *Graefe's Archive Ophthalmology*, volume 222, pages 139–141 (1985); and Kerstetter et al., Prostaglandin $F_{2\alpha}$-1-Isopropylester Lowers Intraocular Pressure Without Decreasing Aqueous Humor Flow, *American Journal of Ophthalmology*, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules may lower IOP, these types of molecules have also been associated with undesirable side effects resulting from topical ophthalmic dosing. Such effects include an initial increase in IOP, breakdown of the blood aqueous barrier and conjunctival hyperemia (Alm, The Potential of Prostaglandin Derivatives in Glaucoma Therapy, *Current Opinion in Ophthalmology*, volume 4, No. 11, pages 44–50 (1993)).

Based on the foregoing, a need exists for the development of molecules that may activate the prostaglandin DP and/or FP receptors, yielding a more efficacious lowering of IOP, while exhibiting fewer or reduced side effects.

An agent which exhibits comparable or improved efficacy, but with reduced side effects when compared to other agents, is said to have an improved therapeutic profile. It is an object of this invention to provide a class of IOP lowering agents with an improved therapeutic profile over endogenous prostaglandins, and methods of their use.

SUMMARY OF THE INVENTION

The present invention is directed to compositions and methods of their use in treating glaucoma and ocular hypertension. In particular, the present invention provides certain classes of substituted tetrahydrofurans which may possess functional DP and/or FP receptor agonist activity, and methods of their use in treating glaucoma and ocular hypertension.

DETAILED DESCRIPTION OF THE INVENTION

It has unexpectedly been found that substituted tetrahydrofurans of the present invention exhibit an improved therapeutic profile in the treatment of glaucoma and ocular hypertension when compared to natural prostaglandins and many of their known analogs. The substituted tetrahydrofurans of the present invention are heptanoic acid derivatives having the following formula (III):

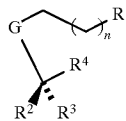

III wherein:
R=ophthalmically acceptable ester moiety, $CO_2R^1$, $CONR^7R^8$, $CH_2OR^9$, or $CH_2NR^{10}R^{11}$ where $R^1$=H, a cationic salt moiety, or an ophthalmically acceptable ammonium moiety; $R^7$ and $R^8$ are the same or different=H or alkyl; $R^9$ =H, acyl, or alkyl; and $R^{10}$ and $R^{11}$ are the same or different=H, acyl, or alkyl; with the proviso that if one of $R^{10}$ and $R^{11}$=acyl, then the other=H or alkyl;
n=0 or 2;
G is:

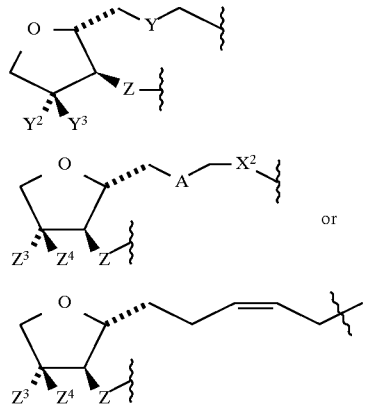

wherein:
Y=$CH_2CH$=$CH$ (cis olefin), $CH$=$CHCH_2$ (cis olefin), or $CH_2CH_2CH_2$;
Z=C≡C, trans CH=CH, or $CH_2CH_2$;
one of $Y^2$ and $Y^3$=H, and the other=halogen or OH, where the OH may be free or functionally modified;

$X^2$=O,S, or $CH_2$;
A=cis CH=CH, $CH_2CH_2$, or C≡C ; and
one of $Z^3$ and $Z^4$=H, and the other=OH, where the OH may be free or functionally modified; or $Z^3$ and $Z^4$ taken together=double bonded O (carbonyl);
one of $R^2$ and $R^3$=H, and the other=F or OH, where the OH may be free or functionally modified; or $R^2$ and $R^3$ taken together=$OCH_2CH_2O$ or double bonded O (carbonyl); and
$R^4$=cyclohexyl, linear or branched $C_5$–$C_7$ alkyl, or $R^5$, wherein:
$R^5$=$(CH_2)_m$Xphenyl or $(CH_2)_pZ^2$, where X=O or $CH_2$; m=1-6; the phenyl is either unsubstituted or substituted with $R^6$, where $R^6$=halogen, $CH_3$, $CF_3$, CN, $OCH_3$ or acetyl; p=0-6; and $Z^2$ =

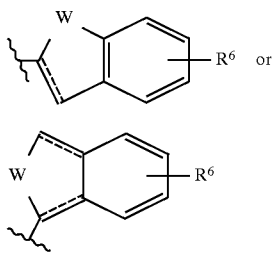

wherein:

W=O, $CH_2$, $CH_2CH_2$, or CH=CH; and $R^6$ is as defined above;

provided that when G is (i) then $R^4$=$R^5$; and when G is (ii) or (iii) then $R^4$=cyclohexyl, linear or branched $C_5$–$C_7$ alkyl, and $R^2$, $R^3$ are different=H and OH.

For purposes of the foregoing definition, the terms "ophthalmically acceptable ester moiety" and "ophthalmically acceptable ammonium moiety" mean any ester or ammonium moiety that would be suitable for ophthalmic application, i.e. non-toxic and non-irritating. Preferred esters are alkyl and alkylcycloalkyl esters of carboxylic acids. Most preferred are $C_2$–$C_5$ alkyl esters of carboxylic acids, and especially isopropyl esters.

With the exception of compounds represented by formulas IV and V, racemic systheses of which have been reported by Vlattas, I. in U.S. Pat. Nos. 3,883,659 and 4,088,779, and Vlattas, et al., *Tetrahedron Letters*, 4455–4458 (1974), the compounds useful in the present invention are believed to be novel.

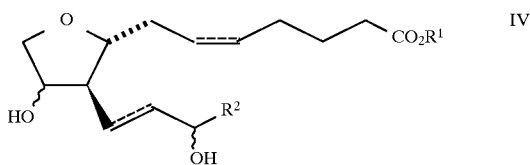

IV wherein:

$R^1$=H; alkali metal, or lower alkyl $R^2$=cyclohexyl; lower alkyl

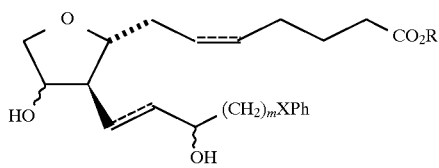

wherein:
R=H, alkali metal, or lower alkyl
phenyl is either unsubstituted or substituted with halogen, $CF_3$, lower alkoxy, lower alkyl
m=1-4
X=$CH_2$ or O In the foregoing illustrations, as well as those provided hereinafter, wavy line attachments indicate that the configuration may be either alpha (α) or beta (β). The dashed lines on bonds between carbons, e.g. in the bicyclic structural formula for $Z^2$, indicate a single or double bond. Two solid lines present between carbons specify the configuration of the relevant double bond. Hatched lines indicate the α configuration, and a solid triangular line indicates the β configuration.

EXAMPLE 1

SYNTHESIS OF Isopropyl [2R(5Z),3S(1E,3R),4S]-7-[Tetrahydro-3-[4-(3-chlorophenoxy)-3-hydroxy-1-butenyl]-4-hydroxy-2-furanyl]-5-heptenoate (VI).

Compound VI may be prepared according to the synthetic route outlined in the following Scheme. The intermediate is prepared from the chiral starting material 1,4-anhydro-D-glucitol, according to the methodology described in Hanessian, et al., *Carbohydrate Research*, 141:221–238 (1985); 1,4-anhydro-D-glucitol itself is conveniently prepared following the procedure of Bock, K. et al., *Acta Chemica Scandinavica B,* 35:441–449 (1981).

Scheme: A Synthetic Route for the Preparation of Compound VI

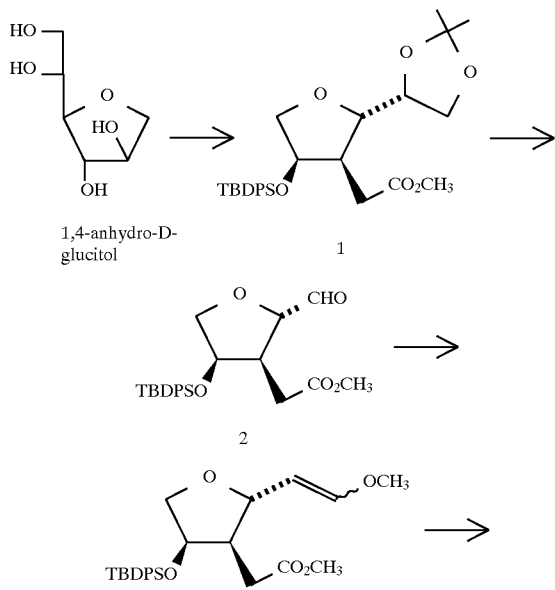

Scheme: A Synthetic Route for the Preparation of Compound VI

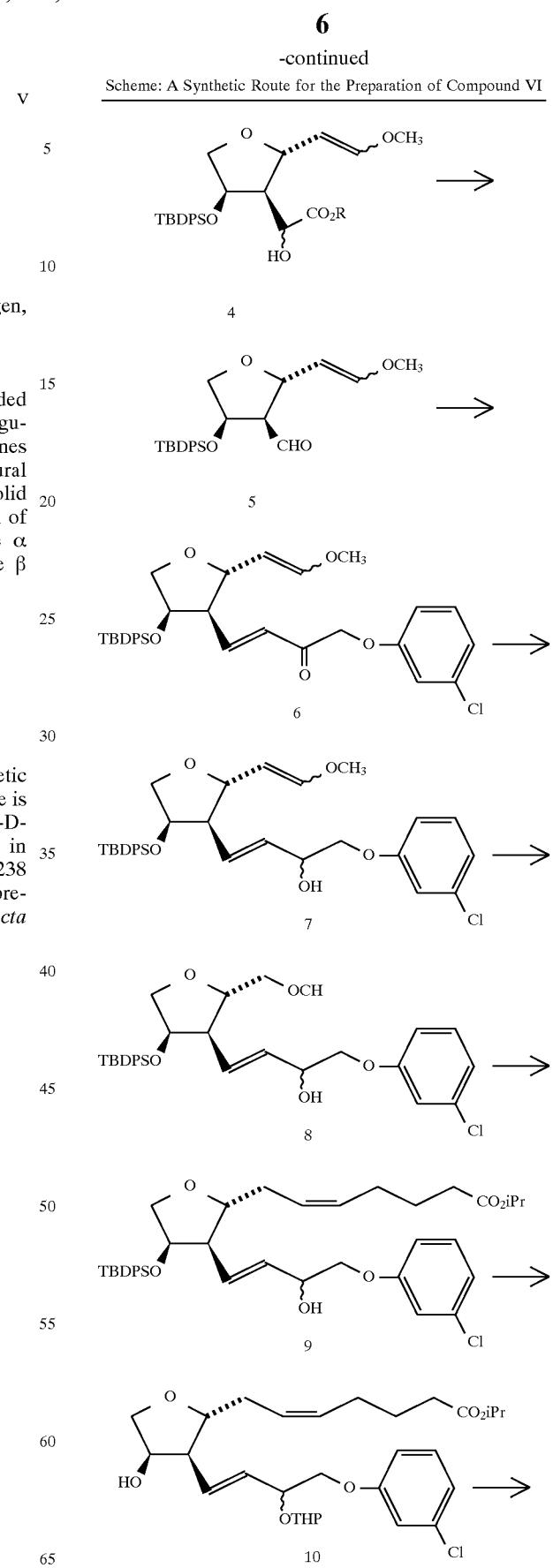

-continued
Scheme: A Synthetic Route for the Preparation of Compound VI

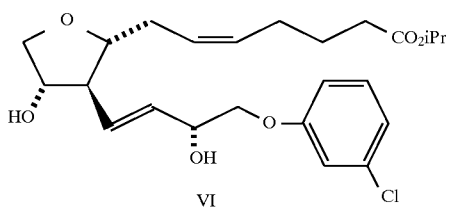

VI

Treatment of compound 1 with $HIO_4$ affords the aldehyde 2 which is then homologated under Wittig reaction conditions to afford the enolether 3. The ester 3 is then reacted with potassium hexamethyldisilazide in THF, and the ester enolate thus formed is quenched with 2-phenylsulfonyl-3-phenyloxaziridine to afford the α-hydroxy methyl ester 4 ($R=CH_3$). Conversion of the ester to the α-hydroxy acid 4 ($R=H$) and reaction of this intermediate carboxylic acid with tetra-n-butylammonium periodate affords the aldehyde 5. Homer-Emmons reaction of 5 with dimethyl-3-(3-chlorophenoxy)-2-oxopropyl-phosphonate affords the enone 6. Reduction of 6 with sodium borohydride in the presence of cerium chloride afford the allylic alcohol 7. Deprotection of the enol ether functionality in 7 under mildly acidic conditions, reaction of the resulting intermediate aldehyde 8 with the ylid derived from (4-carboxybutyl)triphenylphosphonium bromide affords the crude carboxylic acid which is then esterified to the isopropyl ester 9. Protection of the allylic alcohol in 9 as the THP ether, deprotection of the silyl ether with tetrabutylammonium fluoride affords the alcohol 10. Oxidation and reduction of this alcohol function and deprotection of the THP ether under acidic conditions followed by separation of the diastereomers by silica chromatography affords compound VI.

The substituted tetrahydrofurans of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt%) solutions in water at a pH between about 4.5 to about 8.0, preferably between about 5.0 and about 7.5. The compounds are preferably formulated as between about 0.0005 to about 0.03 wt% and, most preferably, between about 0.001 and about 0.01 wt%. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.

Antimicrobial Preservatives:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents:

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-1 03; CREMOPHORE® EL (polyoxyl 35 castor oil); cyclodextrin; or other agents known to those skilled in the art. Such co-solvents are typically employed at a level between about 0.01% and about 2% by weight.

Viscosity Agents:

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of substituted tetrahydrofurans of the present invention include the following Example 2:

EXAMPLE 2

| Ingredient | Amount (wt %) |
| --- | --- |
| Compound VI | 0.01 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor ® EL | 0.1 |
| Benzalkonium chloride | 0.01 |
| HCl and/or NaOH | q.s. pH 7.3–7.4 |
| Purified water | q.s. 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma or ocular hypertension in a patient, which comprises administering to the patient a pharmaceutically effective amount of a compound of the formula following III:

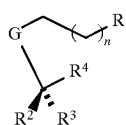

wherein:

R=ophthalmically acceptable ester moiety, $CO_2R^1$, $CONR^7R^8$, $CH_2OR^9$, or $CH_2NR^{10}R^{11}$, where $R^1$=H, a cationic salt moiety, or an ophthalmically acceptable ammonium moiety; $R^7$ and $R^8$ are the same or different=H or alkyl; $R^9$=H, acyl, or alkyl;

and $R^{10}$ and $R^{11}$ are the same or different=H, acyl, or alkyl; with the proviso that if one of $R^{10}$ and $R^{11}$=acyl, then the other=H or alkyl;

n=0 or 2;

G is:

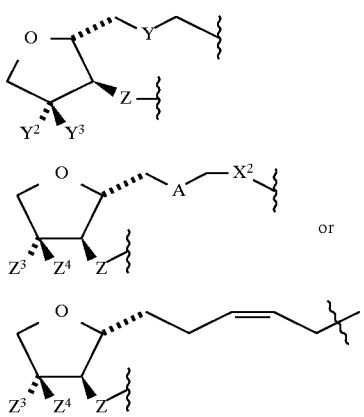

wherein:

Y=cis $CH_2CH$=CH, cis CH=$CHCH_2$, or $CH_2CH_2CH_2$;
Z=C≡C, trans CH=CH, or $CH_2CH_2$;
one of $Y^2$ and $Y^3$=H, and the other=halogen or OH, where the OH may be free or functionally modified;
$X^2$=O, S, or $CH_2$;
A=cis CH=CH, $CH_2CH_2$, or C≡C ; and
one of $Z^3$ and $Z^4$=H, and the other=OH, where the OH may be free or functionally modified; or $Z^3$ and $Z^4$ taken together=double bonded O;
one of $R^2$ and $R^3$=H, and the other=F or OH, where the OH may be free or functionally modified; or $R^2$ and $R^3$ taken together=$OCH_2CH_2O$ or double bonded O; and
$R^4$=cyclohexyl, linear or branched $C_5$–$C_7$ alkyl, or $R^5$, wherein:
$R^5$=$(CH_2)_m$Xphenyl or $(CH_2)_p$ $Z^2$, where X=O or $CH_2$; m=1-6; the phenyl is either unsubstituted or substituted with $R^6$, where $R^6$=halogen, $CH_3$, $CF_3$, CN, $OCH_3$ or acetyl; p=0-6; and $Z^2$ =

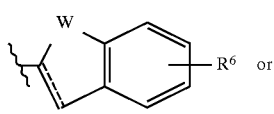 or

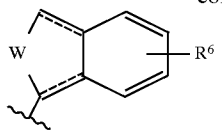

wherein:
W=O,$CH_2$, $CH_2CH_2$, or CH=CH; and $R^6$ is as defined above;
provided that when G is (i) then $R^4$=$R^5$ and when G is (ii) or (iii) then $R^4$=cyclohexyl, linear or branched $C_5$–$C_7$ alkyl, and $R^2$, $R^3$ are different=H, and OH.

2. The method of claim 1, where the compound is administered topically.

3. The method of claim 2, wherein the compound is administered as a solution, suspension, or emulsion.

4. The method of claim 2, wherein G is (i).

5. The method of claim 2, wherein G is (ii).

6. The method of claim 2, wherein G is (iii).

7. The method of claim 4, wherein R is an ophthalmically acceptable ester selected from the group consisting of: isopropyl and neopentyl esters of carboxylic acids.

8. The method of claim 5, wherein R is an ophthalmically acceptable ester selected from the group consisting of: isopropyl and neopentyl esters of carboxylic acids, and $R^4$ is cyclohexyl.

9. The method of claim 6, wherein R is an ophthalmically acceptable ester selected from the group consisting of: isopropyl and neopentyl esters of carboxylic acids, and $R^4$ is cyclohexyl.

10. The method of claim 3, wherein the concentration of the compound is between about 0.00003 to about 0.5 weight percent.

11. The method of claim 10, wherein the concentration of the compound is between about 0.0005 to about 0.03 weight percent.

12. The method of claim 11, wherein the concentration of the compound is between about 0.001 and about 0.01 weight percent.

13. A compound of the following formula III:

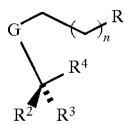

wherein:
R=ophthalmically acceptable ester moiety, $CO_2R^1$, $CONR^7R^8$, $CH_2O R^9$, or $CH_2NR^{10}R^{11}$, where $R^1$=H, a cationic salt moiety, or an ophthalmically acceptable ammonium moiety; $R^7$ and $R^8$ are the same or different=H or alkyl; $R^9$=H, acyl, or alkyl; and $R^{10}$ and $R^{11}$ are the same or different=H, acyl, or alkyl; with the proviso that if one of $R^{10}$ and $R^{11}$=acyl, then the other=H or alkyl;

n=0 or 2;

G is:

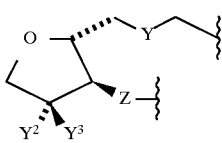

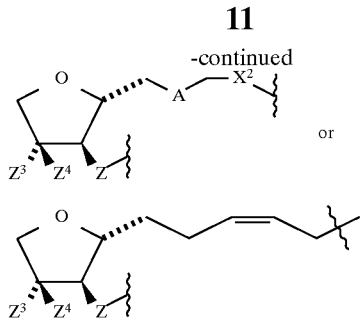

wherein:

Y=cis $CH_2CH=CH$, cis $CH=CHCH_2$, or $CH_2CH_2CH_2$;

Z=C≡C, trans CH=CH, or $CH_2CH_2$;

one of $Y^2$ and $Y^3$=H, and the other=halogen or OH, where the OH may be free or functionally modified;

$X^2$=O or S;

A=cis CH=CH, $CH_2CH_2$, or C≡C; and one of $Z^3$ and $Z^4$=H, and the other=OH, where the OH may be free or functionally modified; or $Z^3$ and $Z^4$ taken together=double bonded O;

one of $R^2$ and $R^3$=H, and the other=F or OH, where the OH may be free or functionally modified; or $R^2$ and $R^3$ taken together=$OCH_2CH_2O$ or double bonded O; and $R^4$=cyclohexyl, linear or branched $C_5$–$C_7$ alkyl, or $R^5$, wherein:

$R^5$=$(CH_2)_m$Xphenyl or $(CH_2)_pZ^2$, where X=O or $CH_2$; m=1-6; the phenyl is either unsubstituted or substituted with $R^6$, where $R^6$=halogen, $CH_3$, $CF_3$, CN, $OCH_3$ or acetyl; p=0-6; and $Z^2$ =

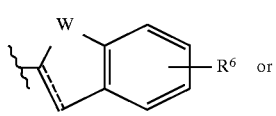 or

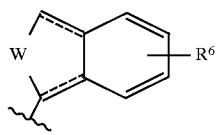

wherein:

W=O, $CH_2$, $CH_2CH_2$, or CH=CH; and $R^6$ is as defined above;

provided that when G is (i) then $R^4$=$R^5$; and when G is (ii) or (iii) then $R^4$=cyclohexyl, linear or branched $C_5$–$C_7$ alkyl, and $R^2$, $R^3$ are different=H, and OH; and further provided that the compounds of the following formula V be excluded:

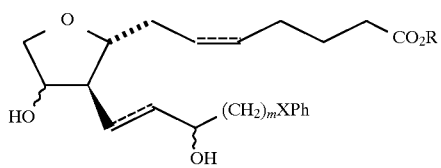

wherein:

R=H, alkali metal, or lower alkyl;

phenyl is either unsubstituted or substituted with halogen, $CF_3$, lower alkoxy, or lower alkyl; and m=1-4 and X=$CH_2$ or O.

14. The compound of claim 13, where G is (i).

15. The compound of claim 13, where G is (ii).

16. The compound of claim 13, wherein G is (iii).

17. An ophthalmic composition for the treatment of glaucoma and ocular hypertension, comprising a compound of formula III:

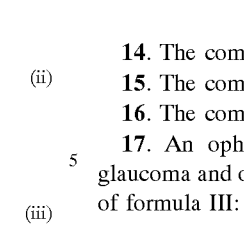 III wherein:

R=ophthalmically acceptable ester moiety, $CO_2R^1$, $CONR^7R^8$, $CH_2OR^9$, or $CH_2NR^{10}R^{11}$, where $R^1$=H, a cationic salt moiety, or an ophthalmically acceptable ammonium moiety; $R^7$ and $R^8$ are the same or different=H or alkyl; $R^9$=H, acyl, or alkyl;

and $R^{10}$ and $R^{11}$ are the same or different=H, acyl, or alkyl; with the proviso that if one of $R^{10}$ and $R^{11}$=acyl, then the other=H or alkyl;

n=0 or 2;

G is:

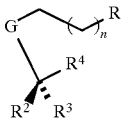 (i)

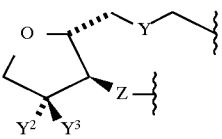 (ii)

or

 (iii)

wherein:

Y=cis $CH_2CH=CH$, cis CH=CHCH$_2$, or $CH_2CH_2CH_2$;

Z=C≡C, trans CH=CH, or $CH_2CH_2$;

one of $Y^2$ and $Y^3$=H, and the other=halogen or OH, where the OH may be free or functionally modified;

$X^2$=O, S, or $CH_2$;

A=cis CH=CH, $CH_2CH_2$, or C≡C; and one of $Z^3$ and $Z^4$=H, and the other=OH, where the OH may be free or functionally modified; or $Z^3$ and $Z^4$ taken together=double bonded O;

one of $R^2$ and $R^3$=H, and the other=F or OH, where the OH may be free or functionally modified; or $R^2$ and $R^3$ taken together=$OCH_2CH_2O$ or double bonded O; and $R^4$=cyclohexyl, linear or branched $C_5$–$C_7$ alkyl, or $R^5$, wherein:

$R^5$=$(CH_2)_m$Xphenyl or $(CH_2)_pZ^2$, where X=O or $CH_2$; m 1-6; the phenyl is either unsubstituted or substituted with $R^6$, where $R^6$=halogen, $CH_3$, $CF_3$, CN, $OCH_3$ or acetyl; p=0-6; and $Z^2 =$

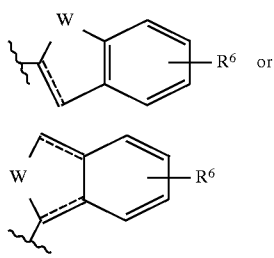

wherein:
W=O, CH$_2$, CH$_2$CH$_2$, or CH=CH; and R$^6$ is as defined above;
provided that when G is (i) then R$^4$=R$^5$; and when G is (ii) or (iii) then R$^4$=cyclohexyl, linear or branched C$_5$–C$_7$ alkyl, and R$^2$, R$^3$ are different=H, and OH;

and pharmaceutically acceptable salts thereof; and an ophthalmically acceptable vehicle therefor.

18. The composition of claim 17, where G is:

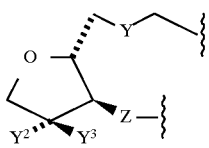

(i)

Y=CH$_2$CH=CH (cis olefin), CH=CHCH$_2$ (cis olefin), or CH$_2$CH$_2$CH$_2$;
Z=C≡C, trans CH=CH, or CH$_2$CH$_2$;

one of Y$^2$ and Y$^3$=H, and the other=halogen or OH, where the OH may be free or functionally modified;

and pharmaceutically acceptable salts thereof; and an ophthalmically acceptable vehicle therefor.

19. The composition of claim 17, wherein G is:

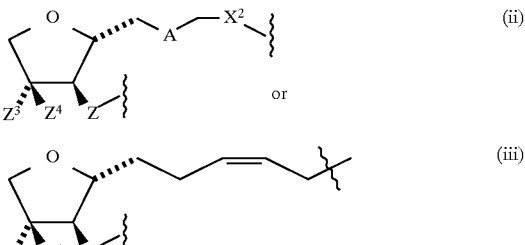

wherein:
X$^2$=O, S, or CH$_2$;
A=cis CH=CH, CH$_2$CH$_2$, or C≡C;
one of Z$^3$ and Z$^4$=H, and the other=OH, where the OH may be free or functionally modified; or Z$^3$ and Z$^4$ taken together=double bonded O (carbonyl);
Z=C≡C, trans CH=CH, or CH$_2$CH$_2$ ;

and pharmaceutically acceptable salts thereof; and an ophthalmically acceptable vehicle therefor.

* * * * *